United States Patent
Venturini et al.

(10) Patent No.: US 7,435,844 B2
(45) Date of Patent: Oct. 14, 2008

(54) ANALOGOUS COMPOUNDS OF STROBILURINES AND THEIR USE AS ACARICIDES AND INSECTICIDES

(75) Inventors: Isabella Venturini, Cameri-Novara (IT); Franco Bettarini, Novara (IT); Paolo Castoro, Vercelli (IT); Alessandro Ciapessoni, Pavia (IT); Marilena Gusmeroli, Monza-Milan (IT); Giovanni Meazza, Saronno-Varese (IT); Domenico Portoso, Lodi (IT); Chiara Sargiotto, Turin (IT)

(73) Assignee: Isagro Ricerca S.r.l., Milan (IT)

( * ) Notice: Subject to any disclaimer, the term of this patent is extended or adjusted under 35 U.S.C. 154(b) by 190 days.

(21) Appl. No.: 10/510,383

(22) PCT Filed: Apr. 11, 2003

(86) PCT No.: PCT/EP03/03784

§ 371 (c)(1),
(2), (4) Date: Mar. 30, 2005

(87) PCT Pub. No.: WO03/087032

PCT Pub. Date: Oct. 23, 2003

(65) Prior Publication Data

US 2006/0235075 A1    Oct. 19, 2006

(30) Foreign Application Priority Data

Apr. 17, 2002    (IT) ............................ MI2002A0814

(51) Int. Cl.
*C07C 69/94*    (2006.01)

(52) U.S. Cl. ............................ 560/60; 560/63; 560/106; 504/239

(58) Field of Classification Search ................. 504/239; 560/60, 63, 106
See application file for complete search history.

(56) References Cited

U.S. PATENT DOCUMENTS

| | | | |
|---|---|---|---|
| 5,021,581 A | * | 6/1991 | Clough et al. ............... 546/309 |
| 5,145,980 A | | 9/1992 | Wenderoth et al. |
| 5,545,664 A | * | 8/1996 | Kirstgen et al. ............. 514/521 |

FOREIGN PATENT DOCUMENTS

| | | | |
|---|---|---|---|
| EP | 89302330.09 | * | 10/1989 |
| EP | 0 398 692 | | 11/1990 |

* cited by examiner

*Primary Examiner*—Yvonne Eyler
*Assistant Examiner*—Yate' K Cutliff
(74) *Attorney, Agent, or Firm*—James V. Costigan; Hedman & Costigan, P.C.

(57) ABSTRACT

Compounds are described, having general formula (I) and their use as acaricides, insecticides and/or fungicides.

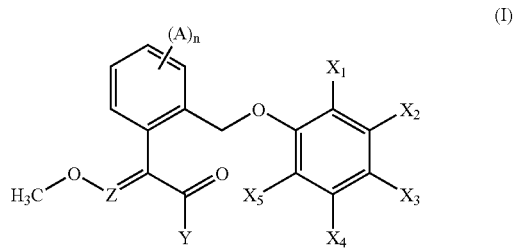

25 Claims, No Drawings

ANALOGOUS COMPOUNDS OF STROBILURINES AND THEIR USE AS ACARICIDES AND INSECTICIDES

The present invention relates to new analogous compounds of strobilurines. More specifically, the present invention relates to new analogous compounds of strobilurines having a high acaricidal and insecticidal activity and their use as acaricides and insecticides.

Analogous products of strobilurines with a fungicidal activity are described in patent applications EP 178826, EP 226917, EP 253213, EP 278595, EP 398692.

Analogous products of strobilurines with an acaricidal and insecticidal activity are described in patent applications EP 242081, EP 299694, EP 335519. In particular, this latter document describes benzyl-phenyl ethers with an acaricidal and insecticidal activity characterized by the presence of the methoxyacrylate group in position 2 of the benzyl group and not more than two substituents on the phenol ring.

The acaricidal/insecticidal activity of the compounds described in the above documents, however, are moderate and cannot be used for practical purposes.

The applicant has now found that in the series of benzyl-phenyl ethers, whose molecular structure is represented by general formula (I), a surprisingly improved acaricidal and insecticidal activity is obtained when a substituent R is present on the phenol ring, as specified below, and at least two of the other four positions are occupied by halogen atoms.

An object of the present invention therefore relates to compounds having general formula (I)

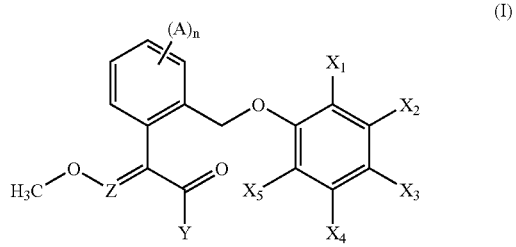

wherein:
a group selected from $X_1$, $X_2$ and $X_3$ represents an R group;
$X_4$ and $X_5$ and two of the remaining $X_1$, $X_2$, $X_3$ groups represent a hydrogen atom or a halogen atom, on the condition that at least two of said groups represent a halogen atom;
R represents a $C_1$-$C_{12}$ alkyl or haloalkyl group; a $C_1$-$C_{12}$ alkoxy or alkylthio group optionally substituted by: halogen atoms, cyano groups, $C_1$-$C_6$ alkoxy groups optionally halogenated, $C_2$-$C_{10}$ alkoxyalkoxy groups optionally halogenated, $NH_2$ groups optionally substituted by $C_1$-$C_6$ alkyl groups optionally halogenated, $C_3$-$C_{12}$ trialkyl silyl groups, aryloxy or heteroaryloxy groups, in turn optionally substituted by halogen atoms, $C_1$-$C_6$ alkyl groups optionally halogenated, $C_1$-$C_6$ alkoxy groups optionally halogenated, nitro groups, cyano groups; a $C_2$-$C_{12}$ alkenyloxy or alkenylthio group optionally substituted by halogen atoms, cyano groups, aryl groups or heteroaryl groups, in turn optionally substituted by halogen atoms, $C_1$-$C_6$ alkyl, halo-alkyl, alkoxy, halo-alkoxy groups, nitro groups, cyano groups; a $C_3$-$C_{12}$ alkynyloxy or alkynylthio group optionally substituted by halogen atoms, $C_1$-$C_6$ alkoxy or haloalkoxy groups, aryl or heteroaryl groups, in turn optionally substituted by halogen atoms, $C_1$-$C_6$ alkyl, haloalkyl, alkoxy, halo-alkoxy groups, nitro groups, cyano groups; a linear or branched $C_3$-$C_{12}$ alkoxyiminoalkylidenoxy or alkoxyiminoalkylidenthio group; a $C_3$-$C_8$ cycloalkoxy or cycloalkylthio group optionally substituted by halogen atoms, $C_1$-$C_6$ alkyl, haloalkyl, alkoxy, haloalkoxy groups; a $C_4$-$C_{12}$ cycloalkylalkoxy or cycloalkylalkylthio group optionally substituted by halogen atoms, $C_1$-$C_6$ alkyl, haloalkyl, alkoxy, haloalkoxy groups; a heterocyclyloxy, heterocyclylthio, heterocyclyl-($C_1$-$C_6$)alkoxy or hetero-cyclyl-($C_1$-$C_6$) alkylthio group, optionally substituted by halogen atoms, ($C_1$-$C_6$) alkyl, haloalkyl, alkoxy, halo-alkoxy groups; an aryloxy, arylthio, heteroaryloxy, heteroarylthio, aryl-($C_1$-$C_6$) alkoxy, aryl-($C_1$-$C_6$) alkylthio, heteroaryl-($C_1$-$C_6$) alkoxy or heteroaryl-($C_1$-$C_6$)alkylthio group optionally substituted by halogen atoms, $C_1$-$C_6$ alkyl groups optionally halogenated, $C_1$-$C_6$ alkoxy groups optionally halogenated, nitro groups, cyano groups;
A, the same or different when n is greater than or equal to 2, represents a halogen atom or a $C_1$-$C_4$ alkyl, haloalkyl, alkoxy, haloalkoxy group;
Y represents an $OCH_3$ group, an $NHCH_3$ group, an $NH_2$ group;
Z represents a CH group or a nitrogen atom N;
n is an integer ranging from 0 to 4.

Preferred compounds having general formula (I) are those wherein $X_3$ represents an R group according to the meanings defined above, $X_2$ and $X_4$ represent a halogen atom, $X_1$ and $X_5$ represent a hydrogen atom and n is equal to 0.

In the meanings defined above, halogen atom refers to a fluorine, chlorine, bromine or iodine atom.

Alkyl group refers to a linear or branched group, such as, for example: a methyl, ethyl, iso-propyl, n-propyl, tert-butyl, iso-butyl, n-butyl, n-pentyl, 2,2-dimethylpropyl, n-decyl group.

Haloalkyl group refers to a linear or branched group such as, for example: a trifluoromethyl, trichloromethyl, 2,2,2-trifluoroethyl, 3,3,3-trifluoropropyl, 2,2,2-trifluoro-1-methylethyl group.

Alkoxy or alkylthio group optionally substituted refers to a linear or branched group such as, for example: a methoxy or methylthio group, a difluoromethoxy or difluormethylthio group, a trifluoromethoxy or trifluoromethylthio group, an ethoxy or ethylthio group, a 2,2,2-trifluoroethoxy or 2,2,2-trifluoroethylthio group, a 2-fluoroethoxy or 2-fluoroethylthio group, a 1,1,2,2-tetrafluoroethoxy or 1,1,2,2-tetrafluoroethylthio group, a 1,2-dichloro-1,2-difluoroethoxy or 1,2-dichloro-1,2-difluoroethylthio group, an n-propoxy or n-propylthio group, an iso-propoxy or iso-propylthio group, a 3-chloropropoxy or 3-chloropropylthio group, a 3,3,3-trifluoropropoxy or 3,3,3-trifluoropropylthio group, a 1,1,2,3,3,3-hexafluoropropoxy or 1,1,2,3,3,3-hexafluoropropylthio group, an n-butoxy or n-butylthio group, an iso-butoxy or iso-butylthio group, a tert-butoxy or tert-butylthio group, an n-pentoxy or n-pentylthio group, a 3-methylbutoxy or 3-methylbutylthio group, a 3,3-dimethylbutoxy or 3,3-dimethylbutylthio, an n-hexyloxy or n-hexylthio group, an n-decyloxy or n-decylthio group, a methoxymethoxy or methoxymethylthio group, an ethoxymethoxy or ethoxymethylthio group, a 2-methoxyethoxy or 2-methoxyethylthio group, a 2-ethoxyethoxy or 2-ethoxyethylthio group, a 2-ethoxypropoxy or 2-ethoxypropylthio group, a 3-methoxyprop-2-yloxy or 3-methoxyprop-2-ylthio group, a 3-ethoxypropoxy or 3-ethoxypropylthio group, a 2-(2-chloroethoxy)ethoxy or 2-(2-chloroethoxy)ethyltio group, a 2-(2-fluoroethoxy) ethoxy or 2-(2-fluoroethoxy)ethyltio group, a 1,1,2-trifluoro-2-trifluoromethoxyethoxy or 1,1,2-trifluoro-2-trifluoromethoxyethylthio group, a 2-(1,1,2,2-tetrafluoroethoxy) ethoxy or 2-(1,1,2,2-tetrafluoroethoxy)ethylthio group, a 2-(2-methoxyethoxy)ethoxy or 2-(2-methoxyethoxy)ethylthio group, a 2-(2-ethoxyethoxy)ethoxy or 2-(2-ethoxyethoxy)ethylthio group, a cyanomethoxy or cyanomethylthio group, a 2-cyanoethoxy or 2-cyanoethylthio group, a 2-aminoethoxy or 2-aminoethylthio group, a 3-aminopropoxy or 3-aminopropylthio group, a 2-(N,N-dimethylamino)ethoxy or 2-(N,N-dimethylamino)ethylthio group, a 2-(N,N-diethylamino)ethoxy or 2-(N,N-diethylamino)ethylthio group, a 3-(N,N-dimethylamino)propoxy or 3-(N,N-dimethylamino)propylthio group, a 2-(N,N-diethylamino)propoxy or 2-(N,N-diethylamino)propylthio group, a 2-(N-ethylamino)-ethoxy or 2-(N-ethylamino)ethylthio group, a trimethylsilylmethoxy or trimethylsilylmethylthio group, a 2-(4-chlorophenoxy)ethoxy or 2-(4-chlorophenoxy)-ethylthio group, a 2-(4-methoxyphenoxy)ethoxy or 2-(4-methoxyphenoxy)ethylthio group, a 2-(4-trifluoromethylphenoxy)ethoxy or 2-(4-trifluoromethylphenoxy)-ethylthio group, a 2-(5-trifluoromethyl-2-pyridyloxy)-ethoxy or 2-(5-trifluoromethyl-2-pyridyloxy)ethylthio group, a 3-(5-trifluoromehtyl-2-pyridyloxy)propoxy or 3-(5-trifluoromethyl-2-pyridyloxy)propylthio group.

An alkenyloxy or alkenylthio group optionally substituted, refers to a linear or branched group such as, for example: a 2-propenyloxy or 2-propenylthio group, a 3-methyl-2-butenyloxy or 3-methyl-2-butenylthio group, a 3,3-dichloro-2-propenyloxy or 3,3-dichloro-2-propenylthio group, a 3-chloro-4,4,4-trifluoro-2-butenyloxy or 3-chloro-4,4,4-trifluoro-2-butenylthio group, a 3,4,4,4-tetrafluoro-2-butenyloxy or 3,4,4,4-tetrafluoro-2-butenylthio group, a 5,5-dichloro-4-pentenyloxy or 5,5-dichloro-4-pentenylthio group, a 3-cyano-2-propenyloxy or 3-cyano-2-propenylthio group, a 3-phenyl-2-propenyloxy or 3-phenyl-2-propenylthio group, a 3-(4-chlorophenyl)-2-propenyloxy or 3-(4-chlorophenyl)-2-propenylthio group.

An alkynyloxy or alkynylthio group optionally substituted, refers to a linear or branched group such as, for example, a 2-propynyloxy or 2-propynylthio group, a 3-butynyloxy or 3-butynylthio group, a 3-butynyl-2-oxy or 3-butynyl-2-thio group, a 3-chloro-2-propynyloxy or 3-chloro-2-propynylthio group, a 4,4,4-trifluoro-2-butynyloxy or 4,4,4-trifluoro-2-butynylthio group, a 5-chloro-4-pentynyloxy or 5-chloro-4-pentynylthio group, a 4-methoxy-2-butynyloxy or 4-methoxy-2-butynylthio group, a 6-methoxy-4-butynyloxy or 6-methoxy-4-butynylthio group, a 3-(4-chlorophenyl)-2-propynyloxy or 3-(4-chlorophenyl)-2-propynylthio group.

An alkoxyiminoalkylidenoxy or alkoxyiminoalkylidenthio group refers to a linear or branched group such as, for example: a 2-methoxyiminoethylidenoxy or 2-methoxyiminoethylidenthio group, a 2-methoxyiminopropylidenoxy or 2-methoxyiminopropylidenthio group.

Examples of cycloalkoxy or cycloalkylthio groups optionally substituted are: a cyclopentoxy or cyclopentylthio group, a cyclohexyloxy or cyclohexylthio group, a 2,2-difluorocyclohexyloxy or 2,2-difluoro-cyclohexylthio group, a 2,6-dimethylcyclohexyloxy or 2,6-dimethylcyclohexylthio group.

Examples of cycloalkylalkoxy or cycloalkylthio groups optionally substituted are: a cyclopropylethoxy or cyclopropylmethylthio group, a 1-cyclopropylethoxy or 1-cyclopropylethylthio group, a 2,2-dichlorocyclopropylmethoxy or 2,2-dichlorocyclopropylmethylthio group, a 2,2-dichloro-1-methylcyclopropylmethoxy or 2,2-dichloro-1-methylcyclopropylmethylthio group, a 2-methylcyclopropylmethoxy or 2-methylcyclopropylmethylthio group, a 2,2-dimethylcyclopropylmethoxy or 2,2-dimethylcyclopropylmethylthio group, a cyclobutylmethoxy or cyclobutylmethylthio group, a cyclohexylmethoxy or cyclohexylmethylthio group.

A heterocyclyl group refers to a mono or polycyclic group with 3-14 members, saturated or unsaturated, optionally benzocondensed but not completely aromatic, consisting of carbon atoms and one or more heteroatoms, the same or different, to be selected from nitrogen, sulfur, oxygen.

Examples of heterocyclyloxy or heterocyclylthio groups optionally substituted, are therefore: a tetrahydrofuranyloxy or tetrahydrofuranylthio group, a tetrahydropyranyloxy or tetrahydropyranylthio group, a tetrahydrothiophenoxy or tetrahydrothiophenylthio group, a 1,3-dioxolanyloxy or 1,3-dioxolanylthio group, a 1,4-dioxanyloxy or 1,4-dioxanylthio group, a 3-piperidinyloxy or 3-piperidinylthio group, a 4-piperidinyloxy or 4-piperidinylthio group, a 1-methyl-3-piperidinyloxy or 1methyl-3-piperidinylthio group.

Examples of heterocyclyl-($C_1$-$C_6$) alkoxy or heterocyclyl-($C_1$-$C_6$)alkylthio groups optionally substituted, are: a glycidyloxy or glycidylthio group, an oxethanylmethoxy or oxethanylmethylthio group, a tetrahydrofuranylmethoxy or tetrahydrofuranylmethylthio group, a tetrahydropyranylmethoxy or tetrahydropyranyl-methylthio group, a tetrahydrothiophenylmethoxy or tetrahydrothiophenylmethylthio group, a 1,3-dioxolanyl-methoxy or 1,3-dioxolanylmethylthio group, a 1,4-dioxanylmethoxy or 1,4-dioxanylmethylthio group, a 1-piperidinylethoxy or 1-piperidinylethylthio group.

An aryl group refers to a mono- or poly-cyclic aromatic carbocyclic group, such as phenyl and naphthyl.

Examples of aryloxy or arylthio groups optionally substituted, are therefore: a phenoxy or phenylthio group, a 4-trifluoromethylphenoxy or 4-trifluoromethylphenylthio group, a 4-chlorophenoxy or 4-chlorophenylthio group, a 4-nitrophenoxy or 4-nitrophenylthio group, a naphthyloxy or naphthylthio group.

A hetero-aryl group refers to a mono or polycyclic aromatic group consisting of carbon atoms and one or more hetero-atoms, the same or different, to be selected from nitrogen, sulfur, oxygen; for example: pyridyl, thiophenyl, furanyl, pyrrolyl, pyrazolyl, pyrimidyl, triazolyl, oxazolyl, isoxazolyl, thiazolyl, isothiazolyl, thiadiazolyl, triazinyl, tetrazinyl, benzoxazolyl.

Examples of hetero-aryloxy or hetero-arylthio groups optionally substituted are therefore: 2-pyridyloxy or 2-pyridylthio, 5-chloro-2-pyridyloxy or 5-chloro-2-pyridylthio, 5-trifluoromethyl-2-pyridyloxy or 5-trifluoromethyl-2-pyridylthio, 5-trifluoromethyl-1,3,4-thiadiazolyloxy or 5-trifluoromethyl-1,3,4-thiadiazolylthio.

Examples of aryl-($C_1$-$C_6$)alkoxy or aryl-($C_1$-$C_6$)alkylthio groups optionally substituted, are: a benzyloxy or benzylthio group, a 4-chlorobenzyloxy or 4-chlorobenzylthio group, a 4-tert-butylbenzyloxy or 4-tert-butylbenzylthio group, a 1-(4-chlorophenyl)ethoxy or 1-(4-chlorophenyl)ethylthio group.

Examples of hetero-aryl-($C_1$-$C_6$)alkoxy or heteroaryl-($C_1$-$C_6$) alkylthio groups optionally substituted, are: 2-furanylmethoxy or 2-furanylmethylthio, 5-nitro-2-furanylmethoxy or 5-nitro-2-furanylmethylthio, 2-thienylmethoxy or 2-thienylmethylthio, 3-pyridylmethoxy or 3-pyridylmethylthio, 6-chloro-3-pyridylmethoxy or 6-chloro-3-pyridylmethylthio.

Although the compounds having general formula (I) partially fall within the scope of the general formulae of patent applications EP 178826, EP 226917, EP 252213, EP 278595 and EP 398692, they are not specifically illustrated therein and are consequently new.

Compounds having formula (I) which are interesting for their biological activity are those described in Examples 1-4 provided further on.

A further object of the present invention relates to the process for the preparation of the compounds having general formula (I).

The compounds having general formula (I) can be obtained by the condensation of a compound having general formula (II) with a phenol having general formula (III), according to reaction scheme 1:

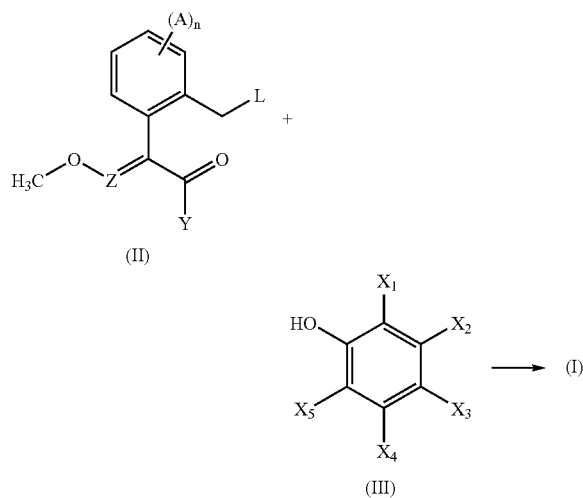

in said formulae, $X_1$, $X_2$, $X_3$, $X_4$, $X_5$, A, Y, Z and n have the meanings defined above, L represents a leaving group such as a chlorine atom, a bromine atom or a $R_L SO_3^-$ group wherein $R_L$ represents a $C_1$-$C_6$ alkyl or haloalkyl, or a phenyl optionally substituted.

The reaction can be conveniently carried out in an inert organic solvent, at a temperature ranging from 0° C. to the boiling point of the reaction mixture, optionally in the presence of an inorganic or organic base.

Preferred solvents for the reaction are alcohols (methanol, ethanol, propanol, methoxyethanol, etc.), ethers (ethyl ether, isopropyl ether, tetrahydrofuran, dioxane, dimethoxyethane, etc.), esters (ethyl acetate, etc.), ketones (acetone, methylethylketone, etc.), chlorinated hydrocarbons (methylene chloride, dichloroethane, chloroform, carbon tetrachloride, etc.), aromatic hydrocarbons (benzene, toluene, xylene, etc.), aliphatic hydrocarbons (hexane, heptane, cyclohexane, etc.), aprotic dipolar solvents (N,N-dimethylformamide, dimethylsulfoxide, sulfolane, etc.).

Preferred inorganic bases are: hydrides, hydroxides, carbonates of alkaline or alkaline-earth metals (sodium, potassium, calcium, etc.).

Preferred organic bases are: pyridine, dimethylaminopyridine, aliphatic amines (diethylamine, triethylamine, etc.), cyclic amines (morpholine, piperidine, diazabicycloundecene, etc.), alcoholates of alkaline metals (sodium methylate, potassium t-butylate, etc.).

The intermediates having general formula (II) are known compounds.

The phenols of general formula (III), when not known in themselves, can be prepared according to methods known in organic chemical practice.

The compounds having general formula (I) wherein Y represents $NH_2$ or $NHCH_3$ can be alternatively prepared by reaction of the corresponding methyl esther [Y=$OCH_3$ in general formula (I)] with ammonia ($NH_3$), or with methylamine ($CH_3NH_2$).

The reaction can be conveniently carried out in an inert organic solvent, at a temperature ranging from 0° C. to the boiling point of the reaction mixture.

Preferred solvents for carrying out the reaction are alcohols (methanol, ethanol, propanol, methoxyethanol, etc.), ethers (ethyl ether, isopropyl ether, tetrahydrofuran, dioxane, dimethoxyethane, etc.), ketones (acetone, methylethylketone, etc.), chlorinated hydrocarbons (methylene chloride, dichloroethane, chloroform, carbon tetrachloride, etc.), aromatic hydrocarbons (benzene, toluene, xylene, etc.), aliphatic hydrocarbons (hexane, heptane, cyclohexane, etc.), aprotic dipolar solvents (N,N-dimethylformamide, dimethylsulfoxide, sulfolane, etc.) or mixtures of these in any ratio.

The compounds having general formula (I) have an geometric isomerism on the C=Z double bond; the use of the compounds having formula (I) as isomeric mixtures in any proportion, as also the production and use of the single E or Z isomers are included in the scope of the present invention. For the purposes of a biological activity E isomers of the compounds of formula (I) are preferred.

The compounds having general formula (I) have a high acaricidal and insecticidal activity which is exerted with respect to the adults, larvae and eggs of mites and insects which are harmful in the agrarian, civil and zoo-technical field.

A further object of the present invention therefore relates to the use of the compounds having general formula (I) as acaricides and/or insecticides and/or fungicides, both in agriculture and other fields. In particular, the use of E isomers of the compounds having formula (I) are preferred.

The use of the compounds having formula (I) wherein $X_3$ represents an R group according to the meanings defined above, $X_2$ and $X_4$ represent a halogen atom, $X_1$ and $X_5$ represent a hydrogen atom and n is equal to 0, is preferred.

Particularly preferred is the use of compounds having formula (I) selected from:

methyl (E)-2-[2-(4-cyclopropylmethoxy-3,5-dichlorophenoxymethyl)phenyl]-3-methoxyacrylate;

methyl (E)-2-[2-(4-cyclopropylmethoxy-3,5-dichlorophenoxymethyl)phenyl]-2-methoxyiminoacetate;

(E)-2-[2-(4-cyclopropylmethoxy-3,5-dichlorophenoxymethyl)phenyl]-N-methyl-2-methoxyiminoacetamide;

methyl (E)-2-{2-[4-(2,2-dichlorocyclopropyl)methoxy-3,5-dichlorophenoxymethyl]phenyl}-3-methoxyacrylate;

methyl (E)-2-{2-[4-(2,2-dichlorocyclopropyl)methoxy-3,5-dichlorophenoxymethyl]phenyl}-2-methoxyiminoacetate;

(E)-2-{2-[4-(2,2-dichlorocyclopropyl)methoxy-3,5-dichlorophenoxymethyl]phenyl}-N-methyl-2-methoxyiminoacetamide;

methyl (E)-2-{2-[3,5-dichloro-4-(3,3-dichloroprop-2-enyloxy)phenoxymethyl]phenyl}-3-methoxyacrylate;

methyl (E)-2-{2-[3,5-dichloro-4-(3,3-dichloroprop-2-enyloxy)phenoxymethyl]phenyl}-2-methoxyiminoacetate;

(E)-2-{2-[3,5-dichloro-4-(3,3-dichloroprop-2-enyloxy)-phenoxymethyl]phenyl)-N-methyl-2-methoxyiminoacetamide;

methyl (E)-2-{2-[3,5-dichloro-4-(3-chloro-4,4,4-trifluorobut-2-enyloxy)phenoxymethyl]phenyl}-3-methoxyacrylate;
methyl (E)-2-{2-[3,5-dichloro-4-(3-chloro-4,4,4-tri-fluorobut-2-enyloxy)phenoxymethyl]phenyl}-2-methoxyiminoacetate;
(E)-2-{2-[3,5-dichloro-4-(3-chloro-4,4,4-tri-fluorobut-2-enyloxy)phenoxymethyl]phenyl}-N-methyl-2-methoxy-iminoacetamide;
methyl (E)-2-[2-(4-cyclobutylmethoxy-3,5-dichlorophenoxymethyl)phenyl]-3-methoxyacrylate;
methyl (E)-2-{2-[3,5-dichloro-4-(3,3-dimethylbutoxy)phenoxymethyl]phenyl}-3-methoxyacrylate;
methyl (E)-2-{2-[3,5-dichloro-4-(3-methylbutoxy)phenoxymethyl]phenyl}-3-methoxyacrylate;
methyl (E)-2-[2-(4-cyclohexylmethoxy-3,5-dichlorophenoxymethyl)phenyl]-3-methoxyacrylate;
methyl (E)-2-{2-[3,5-dichloro-4-(2,4-dichlorobenzyloxy)phenoxymethyl]phenyl}-3-methoxyacrylate;
methyl (E)-2-{2-[3,5-dichloro-4-(4-chlorobenzyloxy)phenoxymethyl]phenyl}-3-methoxyacrylate.

In particular, the compounds having general formula (I) are active against important species of tetranychidae (*Tetranychus urticae, Tetranychus telarius, Tetranychus cinnabarinus, Eotetranychus carpini, Panonychus ulmi, Panonychus citri*, etc.), eriophyidae (*Phytoptus avellanae, Eriophyes vitis, Eriophyes piri*, etc.) tarsonemidae (*Steneotarsonemus pallidus*, etc.), hemiptera (*Macrosiphum euphorbiae, Aphis fabae, Myzus persicae*, etc.), lepidoptera (*Spodoptera* spp., *Heliothis* spp., *Chilo* spp., *Carpocapsa pomonella*, etc.), coleoptera (*Leptinotarsa decemlineata, Phaedon cochleariae*, etc.), diptera (*Aedes* spp., *Culex* spp., *Musca* spp., etc.).

The compounds having general formula (I) also have a good fungicidal activity of both a preventive and curative nature: examples of phytopathogen fungi which can be controlled with the compounds of the invention are: *Helminthosporium* spp., *Erysiphe* spp., *Puccinia* spp., *Plasmopara viticola, Pythium* spp., *Phytophthora* spp., *Rhynchosporium* spp., *Septoria* spp., *Sphaerotheca fuliginea, Podosphaera leucotricha, Pyricularia oryzae, Uncinula necator, Venturia* spp., *Botrytis cinerea, Fusarium* spp., *Alternaria* spp., *Cercospora* spp.

At the same time, the compounds having general formula (I) have a low toxicity with respect to many useful insects and mites, with respect to mammals, fish, birds, and have no phytotoxicity.

Thanks to their positive characteristics, they can be advantageously used in defending not only crops of agrarian and horticultural interest, but also domestic and breeding animals, as well as environments frequented by human beings, from harmful mites, insects and fungi.

The quantity of compound to be applied to obtain the desired effect can vary in relation to various factors such as, for example, the compound used, the crop to be preserved, the type of harmful organism, the degree of infestation, the climatic conditions, the method of application, the formulation adopted.

Doses of compound ranging from 10 g to 5 kg per hectare generally provide a sufficient control.

A further object of the present invention also relates to a method for controlling mites and/or insects and/or phytopathogenic fungi in crops of agrarian and horticultural interest and/or on domestic and breeding animals and/or in environments frequented by human beings, by the application of the compounds having general formula (I). In particular, the quantity of compound to be applied varies from 10 g to 5 kg per hectare.

For practical use in agriculture, it is often useful to use compositions containing one or more compounds having general formula (I).

A further object of the present invention therefore relates to acaricidal and/or insecticidal and/or fungicidal compositions containing one or more compounds having general formula (I) as active principle.

Compositions can be used in the form of dry powders, wettable powders, emulsifiable concentrates, microemulsions, pastes, granulates, solutions, suspensions, etc.: the selection of the type of composition depends on the specific use.

The compositions are prepared in the known way, for example by diluting or dissolving the active substance with a solvent medium and/or a solid diluent, optionally in the presence of surface-active agents.

Solid diluents, or carriers which can be used are, for example: silica, kaolin, bentonite, talc, diatomite, dolomite, calcium carbonate, magnesia, chalk, clays, synthetic silicates, attapulgite, seppiolite.

Liquid diluents which can be used are, for example, in addition to water, aromatic organic solvents (xylols or mixtures of alkylbenzols, chlorobenzene, etc.), paraffins (petroleum fractions), alcohols (methanol, propanol, butanol, octanol, glycerin, etc.), esters (ethyl acetate, isobutyl acetate, etc.), ketones (cyclohexanone, acetone, acetophenone, isophorone, ethylamylketone, etc.), amides (N,N-dimethylformamide, N-methylpyrrolidone, etc.).

Surface-active agents which can be used are salts of sodium, calcium, triethylamine or triethanolamine of alkylsulfonates, alkylarylsulfonates, polyethoxylated alkylphenols, polyethoxylated esters of sorbitol, lignin-sulfonates, etc.

The compositions can also contain special additives for particular purposes, for example adhesion agents such as Arabic gum, polyvinyl alcohol, polyvinyl-pyrrolidone, etc.

The concentration of active principle in the above compositions can vary within a wide range depending on the active compound, the applications for which they are destined, the environmental conditions and the type of formulation adopted. In general the concentration of active principle ranges from 1 to 90%, preferably from 5 to 50%.

If required, it is possible to add to the compositions, other active principles compatible with the compounds having general formula (I), such as, for example, other acaricides/insecticides, fungicides, phyto-regulators, antibiotics, herbicides, fertilizers.

Examples of other acaricides/insecticides which can be added to the above compositions are: abamectin, acephate, acetamiprid, acetoprole, acrinathrin, acequinocyl, alanycarb, aldicarb, allethrin, alpha-cypermethrin, amitraz, azadirachtin, azamethiphos, azinphos-ethyl, azinphos-methyl, azocyclotin, bendiocarb, benfuracarb, bensultap, benzoximate, bifenazate, bifenthrin, bioallethrin, bioresmethrin, bistrifluron, (DBI-3204), bromopropylate, buprofezin, butocarboxim, butoxycarboxim, cadusafos, carbofuran, carbosulfan, cartap, CGA 50439, chinomethionat, chlordane, chlorethoxyfos, chlorfenapyr, chlorfenvinphos, chlorfluazuron, chlormephos, chloropicrin, chlorpyrifos, chlorpyrifos-methyl, chromafenozide, clofentezine, clothianidin, coumaphos, cyanophos, cycloprothrin, cyfluthrin, cyhalothrin, cyhexatin, cypermethrin, cyphenothrin, cyromazine, DDT, deltamethrin, demeton-S-methyl, diafenthiuron, diazinon, dichlorvos, dicofol, dicrotophos, dicyclanil, dienochlor, diflubenzuron, dimethoate, dimethylvinphos, dinobuton, dinocap, dinotefuran (MTI-446), diofenolan, disulfoton, DNOC, indoxacarb, endosulfan, EPN, esfenvalerate, ethiofencarb, ethion, ethiprole, ethoprophos, etofenprox, etoxazole, etrimfos, famphur, fenazaquin, fenbutatin oxide, fenitrothion, fenobucarb, fenothiocarb, fenoxycarb, fenpropathrin, fenpyroximate, fenthion, fenvalerate, fipronil, flucycloxuron, flucythrinate, flufenoxuron, flufenprox, flufenzin, flumethrin, fluvalinate, fonofos, formetanate, formothion, furathiocarb, halfenprox, halofenozide, heptachlor, heptenophos, hexaflumuron, hexythiazox, hydroprene, IKA-2000, IKI-220, imidacloprid, isazofos, isofenphos, isoprocarb, isoxathion, lindane, lufenuron, malathion, mecarbam, methacrifos, methamidophos, methidathion, methiocarb, methomyl, methoprene, methoxychlor, methoxyfenozide, metolcarb, mevinphos, milbemectin, monocrotophos, naled, nicotine, nitenpyran, nithiazine, novaluron, omethoate, oxamyl, oxydemeton-methyl, parathion, permethrin, petroleum oils, phenothrin, phenthoate, phorate, phosalone, phosmet, phosphamidon, phoxim, pirimicarb, pirimiphos-ethyl, pirimiphos-methyl, profenofos, propaphos, propargite, propetamphos, propoxur, prothiofos, protrifenbute, pymetrozine, pyraclofos, pyrethrins, pyridaben, pyridaphenthion, pyrimidifen, pyriproxyfen, quinalphos, rotenone, S-1812, silafluofen, spirodiclofen (BAJ2740), sulfluramid, sulfotep, sulprofos, tar oils, tebufenozide, tebufenpyrad, tebupirimfos, teflubenzuron, tefluthrin, temephos, terbufos, tetrachlorvinphos, tetradifon, tetramethrin, thiacloprid, thiamethoxam, thiocyclam, thiodicarb, thiofanox, thiometon, tolfenpyrad, tralomethrin, transfluthrin, triazamate, triazophos, trichlorfon, triflumuron, trimethacarb, vamidothion, spinosad, vaniliprole, XMC, xylylcarb, ZXI 8901.

Some examples are provided for illustrative purposes but in no way limit the scope of the present invention.

EXAMPLE 1

Preparation of methyl (E)-2-[2-(4-cyclopropylmethoxy-3,5-dichlorophenoxymethyl)phenyl]-3-methoxyacrylate (Compound Nr.1)

A solution of 4-cyclopropylmethoxy-3,5-dichlorophenol (1.54 g; 6.6 mmoles) in DMF (5 ml) is added dropwise, at 0° C., to a suspension of sodium hydride (0.16 g; 6.6 mmoles) in N,N-dimethyl formamide (DMF; 5 ml). The mixture is kept under stirring at room temperature for 30 minutes and a solution of methyl (E)-2-(2bromomethylphenyl)-3-methoxyacrylate (1.9 g; 6.6 mmoles) in DMF (5 ml) is then added. The mixture is kept under stirring for 4 hours; the mixture is diluted with water (40 ml) and an extraction is effected with ethyl acetate (3×25 ml). The organic phases are joined, washed with water (2×20 ml), dried with sodium sulfate, filtered and concentrated at reduced pressure. The raw product obtained is purified by means of silica gel chromatography, eluting with hexane/ethyl acetate 9:1. 1.9 g of the desired product (thick oil) are obtained.

$^1$H-NMR (CDCl$_3$): δ 0.33 (2H, m), 0.61 (2H, m), 1.30 (1H, m), 3.71 (3H, s), 3.78 (2H, d), 3.85 (3H, s), 4.90 (2H, s), 6.82 (2H, s), 7.10-7.55 (4H, m), 7,61 (1H, s).

EXAMPLE 2

Preparation of methyl (E)-2-[2-(4-cyclopropylmethoxy-3,5-dichlorophenoxymethyl)-phenyl]-2-methoxyiminoacetate (Compound Nr.2)

A solution of 4-cyclopropylmethoxy-3,5-dichlorophenol (1.54 g; 6.6 mmoles) in DMF (5 ml) is added dropwise, at 0° C., to a suspension of sodium hydride (0.16 g; 6.6 mmoles) in DMF (5 ml). The mixture is kept under stirring at room temperature for 30 minutes, and a solution of methyl (E)-2-(2-bromomethylphenyl)-3-methoxyiminoacetate (1.9 g; 6.6 mmoles) in DMF (5 ml) is then added. The mixture is kept under stirring for 4 hours; the mixture is diluted with water (40 ml) and an extraction is effected with ethyl acetate (3×25 ml). The organic phases are joined, washed with water (2×20 ml), dried with sodium sulfate, filtered and concentrated at reduced pressure. The raw product obtained is purified by means of silica gel chromatography, eluting with hexane/ethyl acetate 9:1. 1.7 g of the desired product (thick oil) are obtained.

$^1$H-NMR (CDCl$_3$): δ 0.33 (2H, m), 0.61 (2H, m), 1.30 (1H, m), 3.78 (2H, d), 3.85 (3H, s), 4.03 (3H, s), 4.90 (2H, s), 6.82 (2H, s), 7.10-7.55 (4H, m).

EXAMPLE 3

Preparation of (E)-2-[2-(4-cyclopropylmethoxy-3,5-dichlorophenoxymethyl)-phenyl]-N-methyl-2-methoxyiminoacetamide (Compound Nr.3)

A 40% aqueous solution of methylamine (0.8 ml) is added to a solution of methyl (E)-2-[2-(4-cyclopropylmethoxy-3,5-dichlorophenoxymethyl)-phenyl]-2-methoxyiminoacetate (compound nr.2; 0.88 g; 2 mmoles) in DMF (2 ml) and methanol (4 ml). The mixture is kept under stirring for 2 hours at room temperature, diluted with water (40 ml) and an extraction is effected with ethyl acetate (3×25 ml). The organic phases are joined, washed with water (2×20 ml), dried with sodium sulfate and concentrated at reduced pressure. 0.8 g of the product (thick oil) are obtained, which do not require further purification.

$^1$H-NMR (CDCl$_3$): δ 0.33 (2H, m), 0.61 (2H, m), 1.30 (1H, m), 2.90 (3H, d), 3.78 (2H, d), 4.03 (3H, s), 4.90 (2H, s), 6.78 (1H, mb), 6.82 (2H, s), 7.10-7.55 (4H, m).

EXAMPLE 4

Preparation of Compounds Nr.4-146

Operating as described in examples 1-3, the following products were prepared and identified by means of $^1$H-NMR spectroscopy and GC-MS:

methyl (E)-2-[2-(4-cyclopentoxy-3,5-dichlorophenoxymethyl)phenyl]-3-methoxyacrylate (compound Nr.4);

methyl (E)-2-[2-(4-cyclopentoxy-3,5-dichlorophenoxymethyl)phenyl]-2-methoxyiminoacetate (compound Nr.5);

(E)-2-[2-(4-cyclopentoxy-3,5-dichlorophenoxymethyl)phenyl]-N-methyl-2-methoxyiminoacetamide (compound Nr.6);

methyl (E)-2-[2-(4-cyclobutylmethoxy-3,5-dichlorophenoxymethyl)phenyl]-3-methoxyacrilate (compound Nr.7);

methyl (E)-2-[2-(4-cyclobutylmethoxy-3,5-dichlorophenoxymethyl)phenyl]-2-methoxyiminoacetate (compound Nr.8);

(E)-2-[2-(4-cyclobutylmethoxy-3,5-dichlorophenoxymethyl)phenyl]-N-methyl-2-methoxyiminoacetamide (compound Nr.9);

methyl (E)-2-[2-(4-cyclohexyloxy-3,5-dichlorophenoxymethyl)phenyl]-3-methoxyacrylate (compound Nr.10);

methyl (E)-2-[2-(4-cyclohexyloxy-3,5-dichlorophenoxymethyl)phenyl]-2-methoxyiminoacetate (compound Nr.11);

(E)-2-[2-(4-cyclohexyloxy-3,5-dichlorophenoxymethyl) phenyl]-N-methyl-2-methoxyiminoacetamide (compound Nr.12);

methyl (E)-2-[2-(4-cyclohexylmethoxy-3,5-dichlorophenoxymethyl)phenyl]-3-methoxyacrylate, solid with m.p. 103° C.;
$^1$H-NMR(CDCl$_3$): δ 1.22 (5H, m), 1.88 (6H, m), 3.73 (3H, s), 3.74 (2H, d), 3.82 (3H, s), 4.93 (2H, s), 6.84 (2H, s), 7.10-7.55 (4H, m), 7.62 (1H, s). (compound Nr.13);
methyl (E)-2-[2-(4-cyclohexylmethoxy-3,5-dichlorophenoxymethyl)phenyl]-2-methoxyiminoacetate (compound Nr.14);
(E)-2-[2-(4-cyclohexylmethoxy-3,5-dichlorophenoxymethyl)phenyl]-N-methyl-2-methoxyiminoacetamide (compound Nr.15);
methyl (E)-2-[2-(3,5-dichloro-4-methoxyphenoxymethyl)phenyl]-3-methoxyacrylate (compound Nr.16);
methyl (E)-2-[2-(3,5-dichloro-4-metoxyphenoxymethyl)phenyl]-2-methoxyiminoacetate (compound Nr.17);
(E)-2-[2-(3,5-dichloro-4-methoxyphenoxymethyl)phenyl]-N-methyl-2-methoxyiminoacetamide (compound Nr.18);
methyl (E)-2-[2-(3,5-dichloro-4-ethoxyphenoxymethyl)phenyl]-3-methoxyacrylate (compound Nr.19);
methyl (E)-2-[2-(3,5-dichloro-4-ethoxyphenoxymethyl)phenyl]-2-methoxyiminoacetate (compound Nr.20);
(E)-2-[2-(3,5-dichloro-4-ethoxyphenoxymethyl)phenyl]-N-methyl-2-methoxyiminoacetamide (compound Nr.21);
methyl (E)-2-[2-(3,5-dichloro-4-isopropoxyphenoxymethyl)phenyl]-3-methoxyacrylate (compound Nr.22);
methyl (E)-2-[2-(3,5-dichloro-4-isopropoxyphenoxymethyl)phenyl]-2-methoxyiminoacetate (compound Nr.23);
(E)-2-[2-(3,5-dichloro-4-isopropoxyphenoxymethyl)-phenyl]-N-methyl-2-methoxyiminoacetamide (compound Nr.24);
methyl (E)-2-[2-(3,5-dichloro-4-isobutoxyphenoxymethyl)phenyl]-3-methoxyacrylate (compound Nr.25);
methyl (E)-2-[2-(3,5-dichloro-4-isobutoxyphenoxymethyl)phenyl]-2-methoxyiminoacetate (compound Nr.26);
(E)-2-[2-(3,5-dichloro-4-isobutoxyphenoxymethyl)-phenyl]-N-methyl-2-methoxyiminoacetamide (compound Nr.27);
methyl (E)-2-{2-[3,5-dichloro-4-(2,2-dimethylpropoxy)phenoxymethyl]phenyl}-3-methoxyacrylate (compound Nr.28);
methyl (E)-2-{2-[3,5-dichloro-4-(2,2-dimethylpropoxy)phenoxymethyl]phenyl}-2-methoxyiminoacetate (compound Nr.29);
(E)-2-{2-[3,5-dichloro-4-(2,2-dimethylpropoxy)phenoxymethyl]phenyl)-N-methyl-2-methoxyiminoacetamide (compound Nr.30);
methyl (E)-2-{2-[3,5-dichloro-4-(2,2-dimethylethoxy)phenoxymethyl]phenyl)-3-methoxyacrylate (compound Nr.31);
methyl (E)-2-{2-[3,5-dichloro-4-(2,2-dimethylethoxy)phenoxymethyl]phenyl}-2-methoxyiminoacetate (compound Nr.32);
(E)-2-{2-[3,5-dichloro-4-(2,2-dimethylethoxy)phenoxymethyl]phenyl}-N-methyl-2-methoxyiminoacetamide (compound Nr.33);
methyl (E)-2-{2-[3,5-dichloro-4-(3-methylbutoxy)-phenoxymethyl]phenyl}-3-methoxyacrylate, m.p. 70° C.;
$^1$H-NMR(CDCl$_3$): δ 1.0 (6H, d), 1.73 (2H, m), 1.94 (1H, m), 3.73 (3H, s), 3.82 (3H, s), 3.98 (2H, m), 4.93 (2H, s), 6.84 (2H, s), 7.10-7.55 (4H, m), 7.62 (1H, s). (compound Nr.34);
methyl (E)-2-{2-[3,5-dichloro-4-(3-methylbutoxy)-phenoxymethyl]phenyl}-2-methoxyiminoacetate (compound Nr.35);
(E)-2-{2-[3,5-dichloro-4-(3-methylbutoxy)phenoxymethyl]phenyl}-N-methyl-2-methoxyiminoacetamide (compound Nr.36);
methyl (E)-2-[2-(3,5-dichloro-4-hexyloxyphenoxymethyl)phenyl]-3-methoxyacrylate (compound Nr.37);
methyl (E)-2-[2-(3,5-dichloro-4-hexyloxyphenoxymethyl)phenyl]-2-methoxyiminoacetate (compound Nr.38);
(E)-2-[2-(3,5-dichloro-4-hexyloxyphenoxymethyl)phenyl]-N-methyl-2-methoxyiminoacetamide (compound Nr.39);
methyl (E)-2-[2-(3,5-dichloro-4-decyloxyphenoxymethyl)phenyl]-3-methoxyacrylate (compound Nr.40);
methyl (E)-2-[2-(3,5-dichloro-4-decyloxyphenoxymethyl)phenyl]-2-methoxyiminoacetate (compound Nr.41);
(E)-2-[2-(3,5-dichloro-4-decyloxyphenoxymethyl)-phenyl]-N-methyl-2-methoxyiminoacetamide (compound Nr.42);
methyl (E)-2-[2-(3,5-dichloro-4-n-propoxyphenoxymethyl)phenyl]-3-methoxyacrylate (compound Nr.43);
methyl (E)-2-[2-(3,5-dichloro-4-n-propoxyphenoxymethyl)phenyl]-2-methoxyiminoacetate (compound Nr.44);
(E)-2-[2-(3,5-dichloro-4-n-propoxyphenoxymethyl)-phenyl]-N-methyl-2-methoxyiminoacetamide (compound Nr.45);
methyl (E)-2-{2-[3,5-dichloro-4-(2-ethoxyethoxy)-phenoxymethyl]phenyl}-3-methoxyacrylate (compound Nr.46);
methyl (E)-2-{2-[3,5-dichloro-4-(2-ethoxyethoxy)-phenoxymethyl]phenyl}-2-methoxyaminoacetate (compound Nr.47);
(E)-2-{2-[3,5-dichloro-4-(2-ethoxyethoxy)phenoxymethyl]phenyl}-2-methoxyaminoacetamide (compound Nr.48);
methyl (E)-2-{2-[3,5-dichloro-4-(2-methoxyethoxy)-phenoxymethyl]phenyl}-3-methoxyacrylate (compound Nr.49);
methyl (E)-2-{2-[3,5-dichloro-4-(2-methoxyethoxy)-phenoxymethyl]phenyl}-2-methoxyaminoacetate (compound Nr.50);
(E)-2-{2-[3,5-dichloro-4-(2-methoxyethoxy)phenoxymethyl]phenyl}-N-methyl-2-methoxyiminoacetamide (compound Nr.51);
methyl (E)-2-{2-[3,5-dichloro-4-(2-ethoxymethoxy)-phenoxymethyl]phenyl}-3-methoxyacrylate (compound Nr.52);
methyl (E)-2-{2-[3,5-dichloro-4-(2-ethoxymethoxy)-phenoxymethyl]phenyl}-2-methoxyiminoacetate (compound Nr.53);
(E)-2-{2-[3,5-dichloro-4-(2-ethoxymethoxy)-phenoxymethyl]phenyl}-N-methyl-2-methoxyiminoacetamide (compound Nr.54);
methyl (E)-2-{2-[3,5-dichloro-4-(2,2,2-trifluoroethoxy)phenoxymethyl]phenyl}-3-methoxyacrylate (compound Nr.55);
methyl (E)-2-(2-[3,5-dichloro-4-(2,2,2-trifluoroethoxy)phenoxymethyl]phenyl}-2-methoxyiminoacetate (compound Nr.56);
(E)-2-{2-[3,5-dichloro-4-(2,2,2-trifluoroethoxy)-phenoxymethyl]phenyl}-N-methyl-2-methoxyiminoacetamide (compound Nr.57);
methyl (E)-2-[2-(3,5-dichloro-4-trifluoromethoxyphenoxymethyl)phenyl]-3-methoxyacrylate (compound Nr.58);
methyl (E)-2-[2-(3,5-dichloro-4-trifluoromethoxyphenoxymethyl)phenyl]-2-methoxyiminoacetate (compound Nr.59);
(E)-2-[2-(3,5-dichloro-4-trifluoromethoxyphenoxymethyl)phenyl]-N-methyl-2-methoxyiminoacetamide (compound Nr.60);
methyl(E)-2-{2-[3,5-dichloro-4-(1,1,2,2-tetrafluoroethoxy)phenoxymethyl]phenyl}-3-methoxyacrylate (compound Nr.61);

methyl(E)-2-{2-[3,5-dichloro-4-(1,1,2,2-tetrafluoroethoxy) phenoxymethyl]phenyl}-2-methoxyiminoacetate (compound Nr.62);

(E)-2-{2-[3,5-dichloro-4-(1,1,2,2-tetrafluoroethoxy)phenoxymethyl]phenyl}-N-methyl-2-methoxyiminoacetamide (compound Nr.63);

methyl(E)-2-{2-[3,5-dichloro-4-(1,1,2,3,3,3-hexafluoropropoxy)phenoxymethyl]phenyl}-3-methoxyacrylate (compound Nr.64);

methyl(E)-2-{2-[3,5-dichloro-4-(1,1,2,3,3,3-hexafluoropropoxy)phenoxymethyl]phenyl)-2-methoxyiminoacetate (compound Nr.65);

(E)-2-{2-[3,5-dichloro-4-(1,1,2,3,3,3-hexafluoropropoxy) phenoxymethyl]phenyl}-N-methyl-2-methoxyiminoacetamide (compound Nr.66);

methyl(E)-2-{2-[3,5-dichloro-4-(2-trifluoromethoxy-1,1,2-trifluoroethoxy)phenoxymethyl]phenyl}-3-methoxyacrylate (compound Nr.67);

methyl(E)-2-{2-[3,5-dichloro-4-(2-trifluoromethoxy-1,1,2-trifluoroethoxy)phenoxymethyl]phenyl}-2-methoxyiminoacetate (compound Nr.68);

(E)-2-{2-[3,5-dichloro-4-(2-trifluoromethoxy-1,1,2-trifluoroethoxy)phenoxymethyl]phenyl}-N-methyl-2-methoxyiminoacetamide (compound Nr.69);

methyl(E)-2-{2-[3,5-dichloro-4-(2-(2-ethoxyethoxy)-ethoxy)phenoxymethyl]phenyl}-3-methoxyacrylate (compound Nr.70);

methyl(E)-2-{2-[3,5-dichloro-4-(2-(2-ethoxyethoxy)-ethoxy)phenoxymethyl]phenyl}-3-methoxyiminoacetate (compound Nr.71);

(E)-2-{2-[3,5-dichloro-4-(2-(2-ethoxyethoxy)ethoxy)-phenoxymethyl]phenyl}-N-methyl-2-methoxyiminoacetamide (compound Nr.72);

methyl(E)-2-{2-[3,5-dichloro-4-(4-trifluoromethylphenoxy) phenoxymethyl]phenyl}-3-methoxyacrylate (compound Nr.73);

methyl(E)-2-{2-[3,5-dichloro-4-(4-trifluoromethylphenoxy) phenoxymethyl]phenyl}-2-methoxyiminoacetate (compound Nr.74);

(E)-2-{2-[3,5-dichloro-4-(4-trifluoromethylphenoxy)-phenoxymethyl]phenyl}-N-methyl-2-methoxyiminoacetamide (compound Nr.75);

methyl(E)-2-{2-[3,5-dichloro-4-(4-cyanophenoxy)-phenoxymethyl]phenyl}-3-methoxyacrylate (compound Nr.76);

methyl(E)-2-{2-[3,5-dichloro-4-(4-cyanophenoxy)-phenoxymethyl]phenyl}-2-methoxyiminoacetate (compound Nr.77);

(E)-2-{2-[3,5-dichloro-4-(4-cyanophenoxy)phenoxymethyl]phenyl}-N-methyl-2-methoxyiminoacetamide (compound Nr.78);

methyl(E)-2-{2-[3,5-dichloro-4-(4-nitrophenoxy)-phenoxymethyl]phenyl}-3-methoxyacrylate (compound Nr.79);

methyl(E)-2-{2-[3,5-dichloro-4-(4-nitrophenoxy)-phenoxymethyl]phenyl}-2-methoxyiminoacetate (compound Nr.80);

(E)-2-{2-[3,5-dichloro-4-(4-nitrophenoxy)phenoxymethyl] phenyl}-N-methyl-2-methoxyiminoacetamide (compound Nr.81);

methyl(E)-2-[2-(3,5-dichloro-4-benzyloxyphenoxymethyl) phenyl]-3-methoxyacrylate (compound Nr.82);

methyl(E)-2-[2-(3,5-dichloro-4-benzyloxyphenoxymethyl) phenyl]-2-methoxyiminoacetate (compound Nr.83);

(E)-2-[2-(3,5-dichloro-4-benzyloxyphenoxymethyl)-phenyl]-N-methyl-2-methoxyiminoacetamide (compound nr.84);

methyl(E)-2-{2-[3,5-dichloro-4-(4-methoxybenzyloxy)phenoxymethyl]phenyl}-3-methoxyacrylate (compound Nr.85);

methyl(E)-2-{2-[3,5-dichloro-4-(4-methoxybenzyloxy)phenoxymethyl]phenyl}-2-methoxyiminoacetate (compound Nr.86);

(E)-2-{2-[3,5-dichloro-4-(4-methoxybenzyloxy)-phenoxymethyl]phenyl}-N-methyl-2-methoxyiminoacetamide (compound Nr.87);

methyl(E)-2-{2-[3,5-dichloro-4-(4-tert-butyl)benzyloxy) phenoxymethyl]phenyl}-3-methoxyacrylate (compound Nr.88);

methyl(E)-2-{2-[3,5-dichloro-4-(4-tert-butyl)benzyloxy) phenoxymethyl]phenyl}-2-methoxyiminoacetate (compound Nr.89);

(E)-2-{2-[3,5-dichloro-4-(4-tert-butyl)benzyloxy)phenoxymethyl]phenyl}-N-methyl-2-methoxyiminoacetamide (compound Nr.90);

methyl(E)-2-{2-[3,5-dichloro-4-(5-trifluoromethylpyrid-2-yloxy)phenoxymethyl]phenyl}-3-methoxyacrylate (compound Nr.91);

methyl(E)-2-{2-[3,5-dichloro-4-(5-trifluoromethylpyrid-2-yloxy)phenoxymethyl]phenyl}-2-methoxyiminoacetate (compound Nr.92);

(E)-2-{2-[3,5-dichloro-4-(5-trifluoromethylpyrid-2-yloxy) phenoxymethyl]phenyl}-N-methyl-2-methoxyiminoacetamide (compound Nr.93);

methyl(E)-2-{2-[3,5-dichloro-4-(2-propynyloxy)-phenoxymethyl]phenyl}-3-methoxyacrylate (compound Nr.94);

methyl(E)-2-{2-[3,5-dichloro-4-(2-propynyloxy)phenoxymethyl]phenyl}-2-methoxyiminoacetate (compound Nr.95);

(E)-2-{2-[3,5-dichloro-4-(2-propynyloxy)-phenoxymethyl] phenyl}-N-methyl-2-methoxyiminoacetamide (compound Nr.96);

methyl(E)-2-{2-[3,5-dichloro-4-(3-butyn-2-yloxy)-phenoxymethyl]phenyl}-3-methoxyacrylate (compound Nr.97);

methyl(E)-2-{2-[3,5-dichloro-4-(3-butyn-2-yloxy)-phenoxymethyl]phenyl}-2-methoxyiminoacetate (compound Nr.98);

(E)-2-{2-[3,5-dichloro-4-(3-butyn-2-yloxy)phenoxymethyl] phenyl}-N-methyl-2-methoxyiminoacetamide (compound Nr.99);

methyl(E)-2-{2-[3,5-dichloro-4-(3,3-dichloroprop-2-enyloxy)phenoxymethyl]phenyl}-3-methoxyacrylate, thick oil;

$^1$H-NMR(CDCl$_3$): δ 3.74 (3H, s), 3.82 (3H, s), 4.60 (2H, d), 4.93 (2H, s), 6.30 (1H, t), 6.84 (2H, s), 7.10-7.55 (4H, m), 7.62 (1H, s). (compound Nr.100);

methyl(E)-2-{2-[3,5-dichloro-4-(3,3-dichloroprop-2-enyloxy)phenoxymethyl]phenyl}-2-methoxyiminoacetate (compound Nr.101);

(E)-2-{2-[3,5-dichloro-4-(3,3-dichloroprop-2-enyloxy)phenoxymethyl]phenyl}N-methyl-2-methoxyiminoacetamide (compound Nr.102);

methyl(E)-2-{2-[3,5-dichloro-4-(cyanomethoxy)phenoxymethyl]phenyl}-3-methoxyacrylate (compound Nr.103);

methyl(E)-2-{2-[3,5-dichloro-4-(cyanomethoxy)phenoxymethyl]phenyl}-2-methoxyiminoacetate (compound Nr.104);

(E)-2-{2-[3,5-dichloro-4-(cyanomethoxy)phenoxymethyl] phenyl}-N-methyl-2-methoxyiminoacetamide (compound Nr.105);

methyl(E)-2-{2-[2,6-dichloro-4-(2,2-dimethylethyl)phenoxymethyl]phenyl}-3-methoxyacrylate (compound Nr.106);

methyl(E)-2-{2-[2,6-dichloro-4-(2,2-dimethylethyl)phenoxymethyl]phenyl}-2-methoxyiminoacetate (compound Nr.107);

(E)-2-{2-[2,6-dichloro-4-(2,2-dimethylethyl)phenoxymethyl]phenyl}-N-methyl-2-methoxyiminoacetamide (compound Nr.108);

methyl(E)-2-[2-(3-cyclopropylmethoxy-4,6-dichlorophenoxymethyl)phenyl]-3-methoxyacrylate (compound Nr.109);

methyl(E)-2-[2-(3-cyclopropylmethoxy-4,6-dichlorophenoxymethyl)phenyl]-2-methoxyiminoacetate (compound Nr.110);

(E)-2-[2-(3-cyclopropylmethoxy-4,6-dichlorophenoxymethyl)phenyl]-N-methyl-2-methoxyiminoacetamide (compound Nr.111);

methyl(E)-2-{2-[4-(2,2-dichlorocyclopropyl)methoxy-3,5-dichlorophenoxymethyl]phenyl}-3-methoxyacrylate (compound Nr.112);

methyl(E)-2-{2-[4-(2,2-dichlorocyclopropyl)methoxy-3,5-dichlorophenoxymethyl]phenyl}-2-methoxyiminoacetate (compound Nr.113);

(E)-2-{2-[4-(2,2-dichlorocyclopropyl)methoxy-3,5-dichlorophenoxymethyl]phenyl}-N-methyl-2-methoxyiminoacetamide (compound Nr.114);

methyl(E)-2-{2-[3,5-dichloro-4-(3-chloro-4,4,4-trifluorobut-2-enyloxy)phenoxymethyl]phenyl}-3-methoxyacrylate, thick oil,
$^1$H-NMR(CDCl$_3$): δ 3.74 (3H, s), 3.82 (3H, s), 4.72 (2H, m), 4.93 (2H, s), 6.72 (1H, m), 6.84 (2H, s), 7.10-7.55 (4H, m), 7.62 (1H, s). (compound Nr.115);

methyl(E)-2-{2-[3,5-dichloro-4-(3-chloro-4,4,4-trifluorobut-2-enyloxy)phenoxymethyl]phenyl}-2-methoxyiminoacetate (compound Nr.116);

(E)-2-{2-[3,5-dichloro-4-(3-chloro-4,4,4-trifluorobut-2-enyloxy)phenoxymethyl]phenyl}-N-methyl-2-methoxyiminoacetamide (compound Nr.117);

methyl(E)-2-{2-[3,5-dichloro-4-(3-bromo-4,4,4-trifluorobut-2-enyloxy)phenoxymethyl]phenyl}-3-methoxyacrylate (compound Nr.118);

methyl(E)-2-{2-[3,5-dichloro-4-(3-bromo-4,4,4-trifluorobut-2-enyloxy)phenoxymethyl]phenyl}-2-methoxyiminoacetate (compound Nr.119);

(E)-2-{2-[3,5-dichloro-4-(3-bromo-4,4,4-trifluorobut-2-enyloxy)phenoxymethyl]phenyl}-N-methyl-2-methoxyiminoacetamide (compound Nr.120);

methyl(E)-2-{2-[3,5-dichloro-4-(3,4,4,4-tetrafluorobut-2-enyloxy)phenoxymethyl]phenyl)-3-methoxyacrylate (compound Nr.121);

methyl(E)-2-{2-[3,5-dichloro-4-(3,4,4,4-tetrafluorobut-2-enyloxy)phenoxymethyl]phenyl}-2-methoxyiminoacetate (compound Nr.122);

(E)-2-{2-[3,5-dichloro-4-(3,4,4,4-tetrafluoro-but-2-enyloxy)phenoxymethyl]phenyl}-N-methyl-2-methoxyiminoacetamide (compound Nr.123);

methyl(E)-2-{2-[3,5-dichloro-4-(3,3-dibromoprop-2-enyloxy)phenoxymethyl]phenyl)-3-methoxyacrylate (compound Nr.124);

methyl(E)-2-{2-[3,5-dichloro-4-(3,3-dibromoprop-2-enyloxy)phenoxymethyl]phenyl}-2-methoxyiminoacetate (compound Nr.125);

(E)-2-{2-[3,5-dichloro-4-(3,3-dibromoprop-2-enyloxy)phenoxymethyl]phenyl}-N-2-methoxyiminoacetamide (compound Nr.126);

methyl(E)-2-{2-[3,5-dichloro-4-(3,3-difluoroprop-2-enyloxy)phenoxymethyl]phenyl}-3-methoxyacrylate (compound Nr.127);

methyl(E)-2-{2-[3,5-dichloro-4-(3,3-difluoroprop-2-enyloxy)phenoxymethyl]phenyl}-2-methoxyiminoacetate (compound Nr.128);

(E)-2-{2-[3,5-dichloro-4-(3,3-difluoroprop-2-enyloxy)phenoxymethyl]phenyl}-N-methyl-2-methoxyiminoacetamide (compound Nr.129);

methyl(E)-2-{2-[5-(2,2-dichlorocyclopropyl)methoxy-2,4-dichlorophenoxymethyl]phenyl}-3-methoxyacrylate (compound Nr.130);

methyl(E)-2-{2-[5-(2,2-dichlorocyclopropyl)methoxy-2,4-dichlorophenoxymethyl]phenyl}-2-methoxyiminoacetate (compound Nr.131);

(E)-2-{2-[5-(2,2-dichlorocyclopropyl)methoxy-2,4-dichlorophenoxymethyl]phenyl}-N-methyl-2-methoxyiminoacetamide (compound Nr.132);

methyl(E)-2-{2-[4-(2,2-dichlorocyclopropyl)methoxy-2,6-dichlorophenoxymethyl]phenyl}-3-methoxyacrylate (compound Nr.133);

methyl(E)-2-{2-[4-(2,2-dichlorocyclopropyl)methoxy-2,6-dichlorophenoxymethyl]phenyl}-2-methoxyiminoacetate (compound Nr.134);

(E)-2-{2-[4-(2,2-dichlorocyclopropyl)methoxy-2,6-dichlorophenoxymethyl]phenyl}-N-methyl-2-methoxyiminoacetamide (compound Nr.135);

methyl(E)-2-{2-[(2,4-dichloro-5-(3,3-dichloroprop-2-enyloxy)phenoxymethyl]phenyl}-3-methoxyacrylate (compound Nr.136);

methyl(E)-2-{2-[(2,4-dichloro-5-(3,3-dichloroprop-2enyloxy)phenoxymethyl]phenyl}-2-methoxyiminoacetate (compound Nr.137);

(E)-2-{2-[(2,4-dichloro-5-(3,3-dichloroprop-2-enyloxy)phenoxymethyl]phenyl}-N-methyl-2-methoxyiminoacetamide (compound Nr.138);

methyl(E)-2-{2-[(2,6-dichloro-4-(3,3-dichloroprop-2-enyloxy)phenoxymethyl]phenyl}-3-methoxyacrylate (compound Nr.139);

methyl(E)-2-{2-[(2,6-dichloro-4-(3,3-dichloroprop-2-enyloxy)phenoxymethyl]phenyl}-2-methoxyiminoacetate (compound Nr.140);

(E)-2-{2-[(2,6-dichloro-4-(3,3-dichloroprop-2-enyloxy)phenoxymethyl]phenyl}-N-methyl-2-methoxyiminoacetamide (compound Nr.141);

methyl (E)-2-{2-[3,5-dichloro-4-(3,3-dimethylbutoxy)phenoxymethyl]phenyl}-3-methoxyacrylate, m.p. 80° C.,
$^1$H-NMR(CDCl$_3$): δ 1.0 (9H, s), 1.8 (2H, m), 3.73 (3H, s), 3.82 (3H, s), 3.98 (2H, t), 4.93 (2H, s), 6.84 (2H, s), 7.1-7.55 (4H, m), 7.62 (1H, s); (compound Nr.142);

methyl (E)-2-(2-[3,5-dichloro-4-(3,3-dimethylbutoxy)phenoxymethyl]phenyl}-2-methoxyiminoacetate, thick oil, (compound Nr.143);

(E)-2-{2-[3,5-dichloro-4-(3,3-dimethylbutoxy)phenoxymethyl]phenyl}-N-methyl-2-methoxyiminoacetamide, (compound Nr.144);

methyl (E)-2-{2-[3,5-dichloro-4-(2,4-dichlorobenzyloxy)phenoxymethyl]phenyl}-3-methoxyacrylate thick oil, (compound Nr.145);

methyl (E)-2-}2-[3,5-dichloro-4-(4-chlorobenzyloxy)-phenoxymethyl]phenyl}-3-methoxyacrylate, solid with m.p. 112° C., (compound Nr.146).

EXAMPLE 5

Determination of the Acaricidal Activity.

a) Activity Against Adults of *Tetranychus urticae*.

Samples of bean leaves are infested with adult female mites and sprayed, by means of a Potter Tower, with a hydro-acetone solution at 20% by volume of acetone, containing the product being tested at the desired concentration and Tween 20 (0.05%).

The mortality percentage is determined 48 hours after treatment, compared with that of adult mites, by infesting samples only treated with a hydro-acetone solution at 20% by volume of acetone (blank).

The compounds tested provided a full activity at a dose of 500 ppm.

b) Activity Against Eggs and Larvae of *Tetranychus urticae*.

Samples of bean leaves, on which mite eggs were deposited 24 hours before, were sprayed by means of a Potter Tower with a hydro-acetone solution at 20% by volume of acetone, containing the product being tested at the desired concentration and Tween 20 (0.05%).

The percentage of unopened eggs is determined seven days after treatment, compared with that of eggs only treated with a hydro-acetone solution at 20% by volume of acetone (blank).

72 hours after examining the eggs, the mortality percentage of the larvae deriving from the treated eggs is evaluated and compared with that of the larvae deriving from the blank eggs.

The compounds tested provided a full activity at a dose of 200 ppm.

In the claims

1. Compounds having general formula (I)

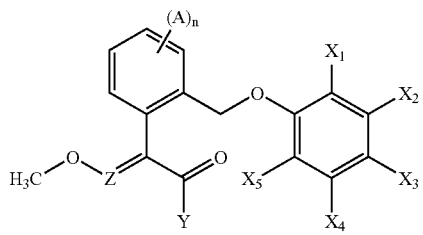

wherein:

a group selected from $X_1$, $X_2$ and $X_3$ represents an R group;

$X_4$ and $X_5$ and two of the remaining $X_1$, $X_2$, $X_3$ groups represent a hydrogen atom or a halogen atom, on the condition that at least two of said groups represent a halogen atom;

R represents a $C_1$-$C_{12}$ alkyl or haloalkyl group; a $C_1$-$C_{12}$ alkoxy or alkylthio group optionally substituted by halogen atoms, cyano groups, $C_1$-$C_6$ alkoxy groups optionally halogenated, $C_2$-$C_{10}$ alkoxyalkoxy groups optionally halogenated, $NH_2$ groups optionally substituted by $C_1$-$C_6$ alkyl groups optionally halogenated, $C_3$-$C_{12}$ trialkyl silyl groups, aryloxy or heteroaryloxy groups, in turn optionally substituted by halogen atoms, $C_1$-$C_6$ alkyl groups optionally halogenated, $C_1$-$C_6$ alkoxy groups optionally halogenated, nitro groups, cyano groups; a $C_2$-$C_{12}$ alkenyloxy or alkenylthio group optionally substituted by halogen atoms, cyano groups, aryl groups or heteroaryl groups, in turn optionally substituted by halogen atoms, $C_1$-$C_6$ alkyl, halo-alkyl, alkoxy, halo-alkoxy groups, nitro groups, cyano groups; a $C_3$-$C_{12}$ alkinyloxy or alkinylthio group optionally substituted by halogen atoms, $C_1$-$C_6$ alkoxy or haloalkoxy groups, aryl or heteroaryl groups, in turn optionally substituted by halogen atoms, $C_1$-$C_6$ alkyl, haloalkyl, alkoxy, halo-alkoxy groups, nitro groups, cyano groups; a linear or branched $C_3$-$C_{12}$ alkoxyiminoalkylidenoxy or alkoxyiminoalkylidenthio group; a $C_3$-$C_8$ cycloalkoxy or cycloalkylthio group optionally substituted by halogen atoms, $C_1$-$C_6$ alkyl, haloalkyl, alkoxy, haloalkoxy groups; a $C_4$-$C_{12}$ cycloalkylalkoxy or cycloalkylalkylthio group optionally substituted by halogen atoms, $C_1$-$C_6$ alkyl, haloalkyl, alkoxy, haloalkoxy groups; a heterocyclyloxy, heterocyclylthio, heterocyclyl-($C_1$-$C_6$) alkoxy or heterocyclyl-($C_1$-$C_6$)alkylthio group, optionally substituted by halogen atoms, ($C_1$-$C_6$) alkyl, haloalkyl, alkoxy, haloalkoxy groups; an aryloxy, arylthio, hetero-aryloxy, heteroarylthio, aryl-($C_1$-$C_6$) alkoxy, aryl-($C_1$-$C_6$)alkylthio, heteroaryl-($C_1$-$C_6$) alkoxy or heteroaryl-($C_1$-$C_6$)alkylthio group optionally substituted by halogen atoms, $C_1$-$C_6$ alkyl groups optionally halogenated, $C_1$-$C_6$ alkoxy groups optionally halogenated, nitro groups, cyano groups;

A, the same or different, when n is greater than or equal to 2, represents a halogen atom or a $C_1$-$C_4$ alkyl, haloalkyl, alkoxyl, haloalkoxyl group;

Y represents an $OCH_3$ group, an $NHCH_3$ group, an $NH_2$ group;

Z represents a CH group;

n is an integer ranging from 0 to 4.

2. The compounds according to claim 1, characterized in that they are an isomeric mixture in any proportion, or the isomer E or the isomer Z of the compounds having formula (I).

3. The compounds according to claim 1, characterized in that they are the isomer E of the compounds having formula (I).

4. The compounds according to claim 1, characterized in that $X_3$ represents an R group according to the above mentioned meanings, $X_2$ and $X_4$ represent a halogen atom, $X_1$ and $X_5$ represent a hydrogen atom and n is equal to 0.

5. Compounds having general formula (I)

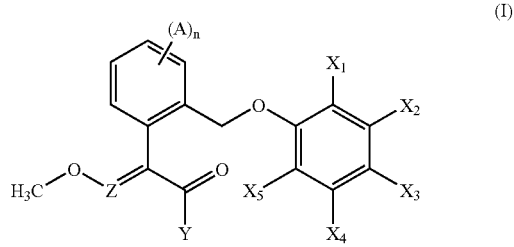

wherein:

a group selected from $X_1$, $X_2$ and $X_3$ represents an R group;

$X_4$ and $X_5$ and two of the remaining $X_1$, $X_2$, $X_3$ groups represent a hydrogen atom or a halogen atom, on the condition that at least two of said groups represent a halogen atom;

R represents a $C_1$-$C_{12}$ alkyl or haloalkyl group; a $C_1$-$C_{12}$ alkoxy or alkylthio group optionally substituted by halogen atoms, cyano groups, $C_1$-$C_6$ alkoxy groups optionally halogenated, $C_2$-$C_{10}$ alkoxyalkoxy groups optionally halogenated, $NH_2$ groups optionally substituted by $C_1$-$C_6$ alkyl groups optionally halogenated, $C_3$-$C_{12}$ trialkyl silyl groups, aryloxy or heteroaryloxy groups, in turn optionally substituted by halogen atoms, $C_1$-$C_6$ alkyl groups optionally halogenated, $C_1$-$C_6$ alkoxy groups optionally halogenated, nitro groups, cyano groups; a $C_2$-$C_{12}$ alkenyloxy or alkenylthio group optionally substituted by halogen atoms, cyano groups, aryl groups or heteroaryl groups, in turn optionally substituted by halogen atoms, $C_1$-$C_6$ alkyl, halo-alkyl, alkoxy, halo-alkoxy groups, nitro groups, cyano groups; a $C_3$-$C_{12}$ alkinyloxy or alkinylthio group optionally substituted by halogen atoms, $C_1$-$C_6$ alkoxy or haloalkoxy groups, aryl or heteroaryl groups, in turn optionally substituted by halogen atoms, $C_1$-$C_6$ alkyl, haloalkyl, alkoxy, halo-alkoxy groups, nitro groups, cyano groups; a linear or branched $C_3$-$C_{12}$ alkoxyiminoalkylidenoxy or alkoxyiminoalkylidenthio group; a $C_3$-$C_8$ cycloalkoxy or cycloalkylthio group optionally substituted by halogen atoms, $C_1$-$C_6$ alkyl, haloalkyl, alkoxy, haloalkoxy groups; a $C_4$-$C_{12}$ cycloalkylalkoxy or cycloalkylalkylthio group optionally substituted by halogen atoms, $C_1$-$C_6$ alkyl, haloalkyl, alkoxy, haloalkoxy groups; a heterocyclyloxy, heterocyclylthio, heterocyclyl-($C_1$-$C_6$) alkoxy or heterocyclyl{$C_1$-$C_6$)alkylthio group, optionally substituted by halogen atoms, ($C_1$-$C_6$)alkyl, haloalkyl, alkoxy, haloalkoxy groups; an aryloxy, arylthio, hetero-aryloxy, heteroarylthio, aryl-($C_1$-$C_6$) alkoxy, aryl-($C_1$-$C_6$)alkylthio, heteroaryl-($C_1$-$C_6$) alkoxy or heteroaryl-($C_1$-$C_6$)alkylthio group optionally substituted by halogen atoms, $C_1$-$C_6$ alkyl groups optionally halogenated, $C_1$-$C_6$ alkoxy groups optionally halogenated, nitro groups, cyano groups;

A, the same or different, when n is greater than or equal to 2, represents a halogen atom or a $C_1$-$C_4$ alkyl, haloalkyl, alkoxyl, haloalkoxyl group;

Y represents an $OCH_3$ group;

Z represents a CH group; n is an integer ranging from 0 to 4.

6. The compounds according to claim 5, characterized in that they are selected from:
methyl (E)-2-[2-(4-cyclopropylmethoxy-3,5-dichlorophenoxymethyl)phenyl]-3-methoxyacrylate;
methyl (E)-2-{2-[4-(2,2-dichlorocyclopropyl)methoxy-3,5-dichlorophenoxymethyl]phenyl}-3-methoxyacrylate;
methyl (E)-2-{2-[3,5-dichloro-4-(3,3-dichloroprop-2-enyloxy)phenoxymethyl]phenyl}-3-methoxyacrylate;
methyl (E)-2-{2-[3,5-dichloro-4-(3-chloro-4,4,4-trifluorobut-2-enyloxy)phenoxymethyl]phenyl}-3-methoxyacrylate;
methyl (E)-2-[2-(4-cyclobutylmethoxy-3,5-dichlorophenoxymethyl)phenyl]-3-methoxyacrylate;
methyl (E)-2-{2-[3,5-dichloro-4-(3,3-dimethylbutoxy)phenoxymethyl]phenyl}-3-methoxyacrylate;
methyl (E)-2-{2-[3,5-dichloro-4-(3-methylbutoxy)phenoxymethyl]phenyl}-3-methoxyacrylate; methyl (E)-2-[2-(4-cyclohexylmethoxy-3,5-dichlorophenoxymethyl]phenyl}-3methoxyacrylate;
methyl (E)-2-{2-[3,5-dichloro-4-(2,4-dichlorobenzyloxy)phenoxymethyl]phenyl}-3-methoxyacrylate;
methyl (E)-2-{-2-[3,5-dichloro-4-(4-chlorobenzyloxy)phenoxymethyl]phenyl}-3-methoxyacrylate.

7. Acaricidal and/or insecticidal and/or fungicidal compositions containing as active principle one or more compounds having general formula (I) according to one of the claims 1-6.

8. The compositions according to claim 7, comprising other active principles compatible with the compounds having general formula (I), such as other acaricides/insecticides, fungicides, phyto-regulators, antibiotics, herbicides, fertilizers.

9. The compositions according to claim 7, characterized in that the concentration of active principle ranges from 1 to 90%, preferably from 5 to 50%.

10. A compound as defined in claim 5 which is methyl (E)-$_2$-{2-[3,5-dichloro-4-(3,3-dimethylbutoxy)phenoxymethyl]phenyl}-3-methoxyacrylate.

11. A method for controlling mites, insects or phytopathogenous fungi in crops of agrarian and horticultural interest, or on domestic and breeding animals, or in environments frequented by human beings, which comprises applying to said mites, insects or phytopathongenous fungi an effective amount of a compound having general formula (I) as in claim 1 wherein: a group selected from $X_1$, $X_2$ and $X_3$ represents an R group; $X_4$ and $X_5$ and two of the remaining $X_1$, $X_2$, $X_3$ groups represents a hydrogen atom or a halogen atom, on the condition that at least two of said groups represent a halogen atom; R represents a $C_1$-$C_{12}$ alkyl or haloalkyl group; a $C_1$-$C_{12}$ alkoxy or alkylthio group optionally substituted by halogen atoms, cyano groups, $C_1$-$C_6$ alkoxy groups optionally halogenated, $C_2$-$C_{10}$ alkoxyalkoxy groups optically halogenated, $NH_2$ groups optionally substituted by $C_1$-$C_6$ alkyl groups optionally halogenated, $C_3$-$C_{12}$ triakyl silyl groups, aryloxy or heteroaryloxy groups, in turn optionally substituted by halogen atoms, $C_1$-$C_6$ alkyl groups optionally halogenated, $C_1$-$C_6$ alkoxy groups optionally halogenated, nitro groups, cyano groups; a $C_2$-$C_{12}$ alkenyloxy or alkenylthio group optionally substituted by halogen atoms, cyano groups, aryl groups or heteroaryl groups, in turn optionally substituted by halogen atoms, $C_1$-$C_6$ alkyl, haloalkyl, alkoxy, halo-alkoxy groups, nitro groups, cyano groups; a $C_3$-$C_{12}$ alkinyloxy or alkinylthio group optionally substituted by halogen atoms, $C_1$-$C_6$ alkoxy or haloalkoxy groups, aryl or heteroaryl groups, in turn optionally substituted by halogen atoms, $C_1$-$C_6$ alkyl, haloalkyl, alkoxy, halo-alkoxy groups, nitro groups, cyano groups; a linear or branched $C_3$-$C_{12}$ alkoxyiminoalkylidenoxy or alkoxyiminoalkylidenthio group; a $C_3$-$C_8$ cycloalkoxy or cycloalkylthio group optionally substituted by halogen atoms, $C_1$-$C_6$ alkyl, haloalkyl, alkoxy, halo-alkoxy groups; a$C_4$-$C_{12}$ cycloalkylalkoxy or cycloalkylalkylthio group optionally substituted by halogen atoms, $C_1$-$C_6$ alkyl, haloalkyl, alkoxy, halo-alkoxy groups; a heterocyclyloxy, heterocyclylthio, heterocyclyl($C_1$-$C_6$)alkoxy or hetero-cyclyl($C_1$-$C_6$)alkylthio group, optionally substituted by halogen atoms, ($C_1$-$C_6$) alkyl, haloalkyl, alkoxy, halo-alkoxy groups; an aryloxy, arylthio, heteroaryloxy, heteroarylthio, aryl-($C_1$-$C_6$)alkoxy, aryl-($C_1$-$C_6$)alkylthio, heteroaryl-($C_1$-$C_6$)alkoxy or heteroaryl-($C_1$-$C_6$)alkylthio group optionally substituted by halogen atoms, $C_1$-$C_6$ alkyl groups optionally halogenated, $C_1$-$C_6$ alkoxy groups optionally halogenated, nitro groups, cyano groups; A, the same or different, when n is greater than or equal to 2, represents a halogen atom or a $C_1$-$C_4$ alkyl, haloalkyl, alkoxyl, haloalkoxy group; Y represents an $OCH_3$ group, an $NHCR_3$ group, an $NH_2$ group; Z represents a CH group; and n is an integer ranging from 0 to 4.

12. The method according to claim 11 of the E isomers of the compounds having formula (I).

13. The method according to claim 11, wherein $X.sub.3$ represents an R group according to the above meanings, $X_2$ and $X_4$ represent a halogen atom, $X_1$ and $X_5$ represent a hydrogen atom and n is equal to 0.

14. The use method according to claim 11, wherein the compounds of formula (I) are selected from: methyl (E)-2-[2-(4-cyclopropylmethoxy-3,5-dichlorophenoxymethyl)

phenyl]-3-methoxyacrylate; methyl (E)-2-{2-[4-(2,2-dichlorocyclopropyl)methoxy-3,5-dichlorophenoxymethyl]phenyl}-3-methoxyacrylate; methyl (E)-2-{2-[3,5-dichloro-4-(3,3-dichloroprop-2-enyloxy)phenoxymethyl]phenyl-}3-methoxyacrylate; methyl (E)-2-{2-[3,5-dichloro-4-(3-chloro-4,4,4-trifluorobut-2-enyloxy)phenoxymethyl]phenyl}-3-methoxyacrylate; methyl (E)-2-[2-(4-cyclobutylmethoxy-3,5-dichlorophenoxymethyl)phenyl]-3-methoxyacrylate; methyl (E)-2-{2-[3,5-dichloro-4-(3,3-dimethylbutoxy)phenoxymethyl]phenyl}-3-methoxyacrylate; methyl (E) -2-{2-[3,5-dichloro-4-(3-methylbutoxy)phenoxymethyl]phenyl}-3-methoxyacrylate; methyl (E)-2-[2-(4-cyclohexylmethoxy-3,5-dichlorophenoxymethyl]phenyl}-3-methoxyacrylate; methyl (E)-2-{2-[3,5-dichloro-4-(2,4-dichlorobenzyloxy)phenoxymethy]phenyl}-3-methoxyacrylate; or methyl (E)-2-{2-[3,5-dichloro-4-(4-chlorobenzyloxy)phenoxymethyl]phenyl}-3-methoxyacrylate.

15. The method according to any of the claims 11-14 for the control of adults, larvae and eggs of mites and insects which are harmful in the agrarian, civil and zoo-technical field.

16. The use method according to claim 15, wherein the harmful mites and/or insects are tetranychidae (*Tetranychus urticae, Tetranychus telarius, Tetranychus cinnabarinus, Entetranychus carpini, Panonychus ulmi, Panonychus citri*, etc.). eriophyidae (*Phytoptus avellanae, Eriophyes vitis, Eriophyes piri*, etc.) tarsonemidae (*Steneotarsonemus pallidus*, etc.), hemiptera (*Macrosiphum euphorbiae, Aphis fabae, Myzus persicae*, etc.), lepidoptera (*Spodoptera* spp., *Heliotbis* spp., *Chilo* spp., *Carpocapsa pornonella*, etc.), coleoptera (*Leptinotarsa decemlineata, Phaedon cochleariae*, etc.), diptera (*Aedes* spp., *Culex* spp., *Musca* spp., etc.).

17. The method according to any of the claims 11-14 for the control of phytopathogenous fungi such as: *Helminthosporium* spp., *Erysiphe* spp., *Puccinia* spp., *Plasmopara viticola, Pythium* spp., *Phytophthora* spp., *Rhynchosporium* spp., *Septoria* spp., *Sphaerotheca fuliginea, Podosphaera leucotricha, Pyricularia oryzae, Uncinula necator, Veinuria* spp., *Botrytis cinerea, Fusarium* spp., *Alternaria* spp., *Cercospora* spp.

18. The method according to any of the claims 11-14 for the control of mites, insects and fungi which are harmful in crops of agrarian and horticultural, interest, on domestic and breeding animals, in environments frequented by human beings.

19. A method for controlling mites and/or insects and/or phytopathogenous fungi in crops of agrarian and horticultural interest, and/or on domestic and breeding animals, and/or in environments frequented by human beings, by the application of die compounds having general formula (I) according to one of the claims 1-4 and 6.

20. The method according to claim 19, characterized in that the quantity of compound to be applied varies from 10 g to 5 kg per hectare.

21. A process for the preparation of the compounds having general formula (I), according to any of the claims 1-4, 6 characterized in that it includes a condensation reaction of a compound having general formula (II) with a phenol having general formula (III), according to the reaction scheme 1:
wherein, $X_1, X_2, X_3, X_4, X_S, A, Y, Z$ and n have the meanings defined above, L represents a leaving group such as a chlorine atom, a bromine atom or a $R_L SO_3$—group wherein $R_L$ represents a $C_1$-$C_6$ alkyl or haloalkyl, or a phenyl optionally substituted.

22. The process according to claim 5, characterized in that the reaction is carried out in an inert organic solvent, at a temperature ranging from 0° C. and the boiling temperature of the reaction mixture, optionally in the presence of an inorganic or organic base.

23. The process according to claim 22, characterized in that the solvent is selected from alcohols, ethers, esters, ketones, chlorinated hydrocarbons, aromatic hydrocarbons, aliphatic hydrocarbons, aprotic dipolar solvents.

24. The process according to claim 22, characterized in that the inorganic base is selected from hydrides, hydroxides, carbonates of alkaline or alkaline-earth metals.

25. The process according to claim 22, characterized in that the organic base is selected from pyridine, dimethylaminopyridine, aliphatic amines, cyclic amines, alcoholates of alkaline metals.

* * * * *